United States Patent [19]

McBride et al.

[11] 4,220,863
[45] Sep. 2, 1980

[54] DATA CHANNEL MULTIPLEXING SYSTEM FOR CT SCANNER WITH ROTATING SOURCE

[75] Inventors: Thomas R. McBride, Chardon; Robert H. Wake, Warrensville Heights; Robert H. McCarthy, Willowick, all of Ohio

[73] Assignee: Ohio Nuclear, Inc., Solon, Ohio

[21] Appl. No.: 783,732

[22] Filed: Apr. 1, 1977

[51] Int. Cl.² .......................................... G03B 41/16
[52] U.S. Cl. ............................. 250/445 T; 250/369; 250/388
[58] Field of Search ................... 250/445 T, 401, 402, 250/360, 363, 366, 369, 385, 388

[56] References Cited
U.S. PATENT DOCUMENTS

| 3,940,626 | 2/1976 | Hounsfield | 250/369 |
| 3,973,128 | 8/1976 | LeMay | 250/445 T |
| 3,996,467 | 12/1976 | Troggatt | 250/445 T |
| 4,031,395 | 6/1977 | LeMay | 250/445 T |

Primary Examiner—Craig E. Church
Attorney, Agent, or Firm—Fay & Sharpe

[57] ABSTRACT

A CT scanner has an outer circular array of stationary radiation detectors for an inner concentrically revolving source of radiation emitted in a fan pattern subtending a number of the detectors. A number of analog signal processing channels equal to the maximum number of subtended detectors at any given time is automatically connected via switching circuitry to receive the outputs of only the detectors within the fan pattern.

5 Claims, 4 Drawing Figures

DATA CHANNEL MULTIPLEXING SYSTEM FOR CT SCANNER WITH ROTATING SOURCE

BACKGROUND OF THE INVENTION

The invention relates generally to the field of radiation imaging of internal structures and more specifically to computerized transaxial tomographic (CT) X-ray scanners. Unlike conventional exposed film X-ray apparatus, the CT scanner produces narrow beams of radiation, either X-rays or gamma rays, through plural coplanar paths defining a cross-sectional or tomographic view of the patient's internal organs such as the brain or the thoracic region. The attenuated beams are sensed by radiation detectors whose electrical output is indicative of the intensity of the radiation received by the detector. One of the early types of CT scanners referred to in the patent literature is shown for example in Hounsfield U.S. Pat. No. 3,778,614. This system is generally referred to in the art as the "translate and rotate" system. A source and a single detector, for example, are aligned opposite each other on a mechanism which causes the beam path between the source and detector to move laterally across the scan circle. After rotating the source/detector carriage assembly to a new orientation, the translational scan is repeated. Readings are taken at uniformly spaced parallel beam locations and representative values are digitally stored. Data from a full set of scans involving numerous relocations of the beam path is manipulated according to known mathematics involving "back projections" to arrive at a digital representation of the tomographic image. This digital representation is converted to a tomogram which can be viewed on a cathode ray tube. Ohio-Nuclear, Inc. markets a type of translate and rotate CT scanner under the trademark "Delta Scan".

The major disadvantage of the translate and rotate system is slowness of the scan mechanism due to the different alternating types of motion. The major advantages of the translate and rotate system are due to the fact that a single detector scans across the entire scan circle thus enabling sampling at any time and avoiding the need to have matched detectors or gain matching.

Another type of scan technique called "purely rotational" employs a fan beam source with a subtended detector array in a fixed relationship such that the fan beam and detector array rotate with each other. This system has a major disadvantage. Numerous detectors are required and none scans across the entire patient. Thus the sampling resolution is lowered and gain matching of the detectors is required. The major advantage of the purely rotational system is its high scanning speed. The high speed of the scanning motion is desirable to avoid the effect on the image of the resultant displacement of organs due to a patient's breathing.

It has been found that computer image reconstruction can be accomplished with yet another arrangement of source and detectors. In this new system the detector array is a *stationary* arc of uniformly spaced detectors about the center point in the scan circle. The fan beam source revolves about the center point inside the detector array irradiating the scan circle and subtending at any given time only a fraction of the detectors in the total array. If desired the array may be a complete circle or ring. The reconstruction algorithms are described in Lakshminarayanan, "Reconstruction from Divergent Ray Data", Technical Report No. 92, State University of New York at Buffalo, Computer Sciences Department, January 1975.

The new type of scanning system, although requiring numerous detectors and somewhat more elaborate digital processing for reconstructing an image, provides the advantage of high scanning speed due to the single mechanical motion of rotation while also providing the capability of achieving high sampling resolution and avoiding gain matching requirements because each detector views the source across the entire scan circle.

SUMMARY OF THE INVENTION

In an arrangement of the above described new type in which a stationary array of spaced detectors receives a fan beam of radiation from a revolving source, the general purpose of the present invention is to apply the outputs of detectors irradiated by the fan beam to a set of signal processing channels without providing a respective exclusive signal processing channel for each of the detectors in the array. This object is accomplished by using a specially designed data channel multiplexing system for use with a CT scanner having a series of stationary radiation detectors spaced in a curved path about a center point and a concentrically rotating source of radiation emitted in a fan pattern subtending a number of the detectors. The irradiated area common to different positions of the fan pattern defines a corresponding patient scan circle. A number of signal processing channels corresponding to the maximum number of detectors subtended by the fan pattern at any given time is connected via switching circuitry to receive the outputs of only the irradiated detectors. This is accomplished in one embodiment by providing a shift register including a series of detector bits, initially loading a predetermined binary number (e.g., all "1's") into a number of consecutive bits of said shift register corresponding to the maximum number of detectors subtended by the radiation fan and then clocking or shifting the shift register bits collectively each time the source advances so that it irradiates another peripheral detector. A number of gate means or switching circuits corresponding to the maximum number of detectors subtended by the fan pattern is connected to receive the outputs of a respective exclusive group of nonconsecutive detectors, one and only one of which is irradiated at any given time by the radiation fan. For any given position of the source, each gate means permits the passage of the output of only the one irradiated detector as determined by the state of the shift register detector bits corresponding respectively to the detectors in the group received by the particular gate means.

DESCRIPTION OF THE PREFERRED EMBODIMENTS

Figure 1:
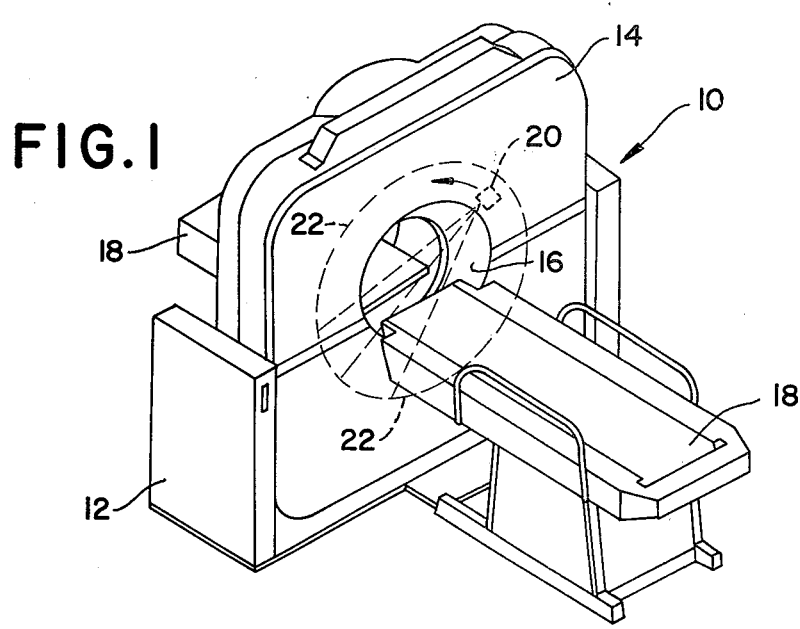
FIG. 1 is a perspective view of a CT scanner assembly.

FIG. 1 illustrates the mechanical apparatus associated with the rotating source type CT scanner system. A gantry assembly 10 includes a U-shaped frame 12 pivotally supporting a gantry 14 having a central circular opening 16 through which a patient is inserted for a body scan, for example, on a two-piece patient table 18. Shown in phantom, the source 20 produces radiation in a coplanar fan beam pattern directed towards the opposite side of the opening 16 and intersecting the center of the opening 16. Mechanisms within the gantry 14 rotate the source 20 counterclockwise about an axis through the center of the opening 16 perpendicular to the fan beam. A ring of detectors 22, also shown in phantom in FIG. 1 is disposed within the gantry 14 concentrically to the opening 16 and at a somewhat greater radius from the center of the opening 16 than the detector ring 22. The detector ring 22 lies in the same plane as the fan beam.

Figure 2:
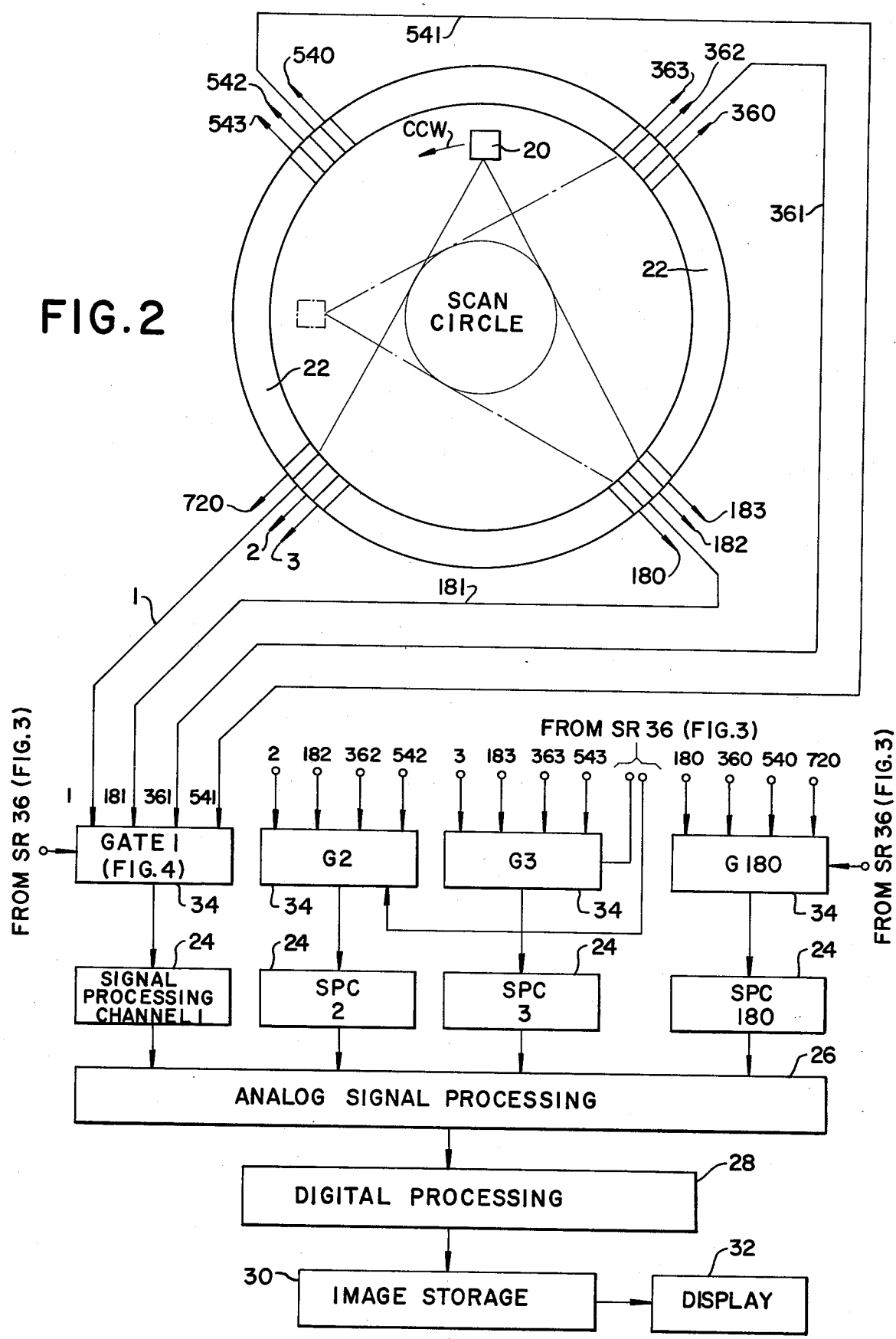
FIG. 2 is a block and schematic diagram of the signal processing channel multiplexing system for a rotating-source-type CT scanner according to the invention.

FIG. 2 shows a system having a full complement of 720 detectors spaced at ½ degree intervals around the detector ring 22. Only certain ones of the detectors are indicated schematically for convenience. Beginning in the middle of the lower left-hand quadrant of the detector ring as viewed in FIG. 2 the detectors are numbered consecutively from 1 to 720 counterclockwise. The rotating source 20 is shown in FIG. 2 in its initial position at the start of the scan. The fan beam width of the radiation produced by the source 20 is such that at any given time it subtends 90 degrees of arc of the detector ring 22 thus irradiating 180 detectors or ¼ of the total number of detectors. The scan circle shown in FIG. 2 is determined as the area common to different positions of the fan pattern. A second position of the source 20 is shown in phantom after rotation about the center of the scan circle through an arc of 90 degrees. At this point the fan beam subtends detectors 181 through 360, still, however, covering only ¼ of the total number of detectors in the detector ring 22. The fraction of detectors irradiated at any given time signifies the reduction in electronic processing channels that is possible.

Since at any given position of the source 20, only ¼ of the full complement of detectors is producing meaningful data, there is no need to process the signals from the other three quarters at the same time. For the embodiment of FIG. 2 only 180 channels of signal processing electronics is necessary instead of 720.

180 identical signal processing channels 24 are provided for a corresponding analog signal processing system 26. The output is digitized and passed for digital processing into reconstructed image data in digital processing system 28. The reconstructed image data is stored in image storage 30 which is ultimately read out to a conventional display 32.

Access to each signal processing channel 24 is shared by four corresponding detectors whose outputs are fed to a corresponding gate or passing means 34. There are 180 gates 34 for the respective 180 signal processing channels 24. Each gate 34 receives outputs from four detectors spaced by 90 degrees from each other. For example, gate No. 1 is connected to receive the outputs of detectors 1, 181, 361 and 541. Gate No. 2 is connected to receive the outputs of detectors 2, 182, 362 and 542. Gate No. 3 is connected to receive the outputs of detectors, 3, 183, 363 and 543 and so on up to gate No. 180 which is connected to receive the outputs of detectors 180, 360, 540 and 720.

The number of signal processing channels, of course, depends on the maximum number of detectors subtended at any given time by the radiation fan produced by the source 20. For example, if there is a full complement of detectors spaced about 360 degrees of arc, and the radiation fan subtends p detectors, there will be p processing channels and p associated gates 34. The number of detector outputs per gate 34 will correspond to the fraction n/p. In the case shown in FIG. 2, n is 720 and p is 180 and n/p is 4.

Figure 3:
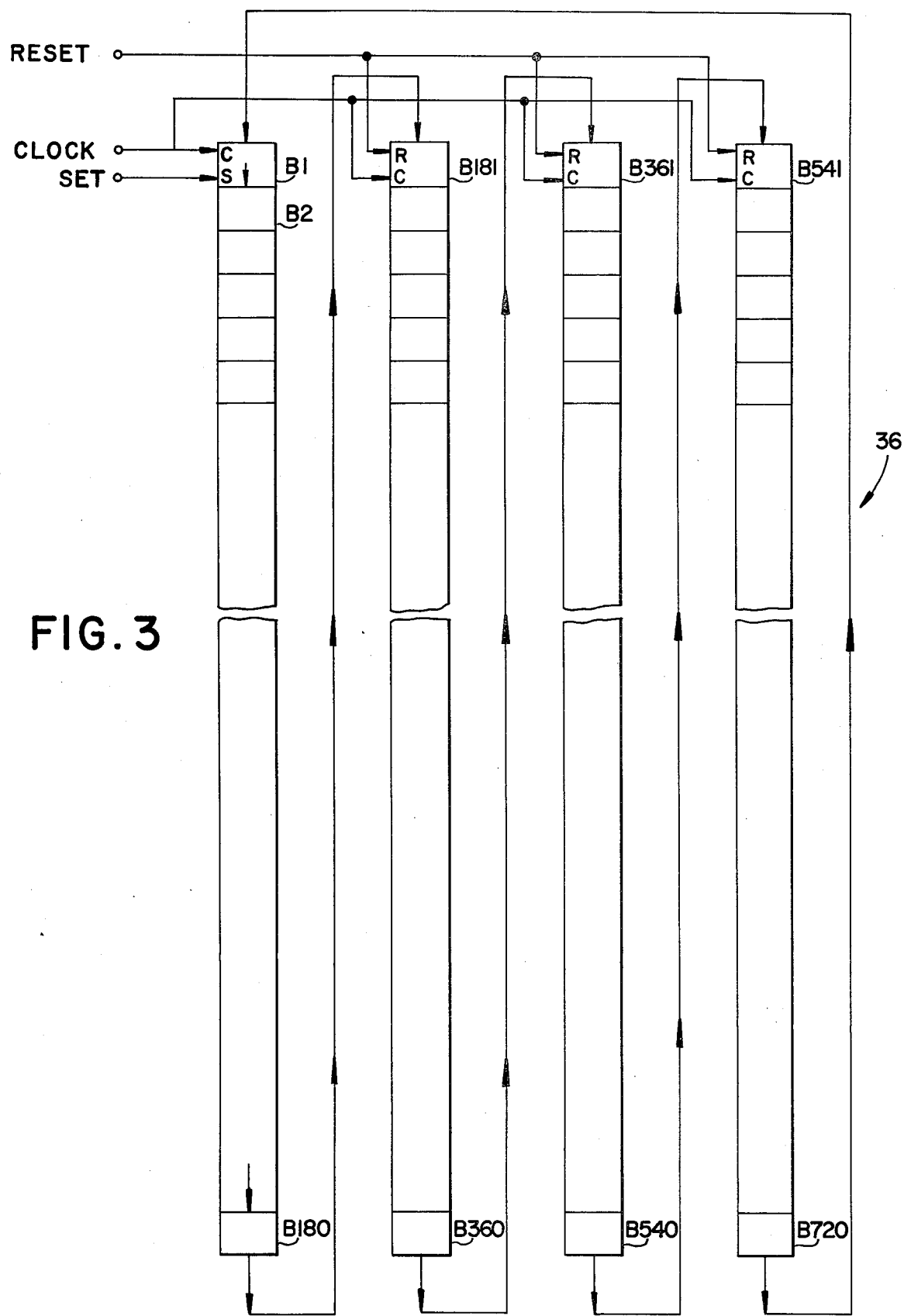
FIG. 3 is a block diagram of a closed loop shift register for circulating detector bits according to the invention.

The gates 34 receive timing signals from a shift register 36 shown in FIG. 3 which determines in each case which one of the four detector output signals to pass to the corresponding signal processing channel. Depending on the input from the shift register 36, gate No. 1 will choose to pass the output of detector 1, 181, 361 or 541 to signal processing channel No. 1. At the same time, gates 2 through 180 will all choose one of the four respective detector output signals to pass to the corresponding signal processing channel. For example in the position of the source 20 shown in FIG. 2, since detectors 1 through 180 are all active, gates Nos. 1 through 180 will choose to pass the outputs of detectors 1 through 180 to the respective processing channels.

The shift register 36 in FIG. 3 is a four-stage 720 bit closed loop shift register comprising four 180 bit registers connected end to end. The output of the last bit of one stage goes to the input of the first bit of the next stage. This closed loop arrangement is not essential, since the input to the first stage can be connected to additional control circuitry which determines when the source is in its initial position.

The consecutive bit positions of the first stage are designated B1, B2 through B180. The bits of the second stage are designated B181 through B360. The bits of the third stage are designated B361 through B540 and the bits of the final stage are designated B541 through B720. Each stage of the shift register 36 has a clock input C. A clock pulse on input C causes all of the bits in that stage to shift to the next bit position. The first stage has a common set input S. A set pulse to the set input S causes all of the bits B1 through B180 to assume binary state "1". The remaining stages do not have set inputs in use. Rather, they have reset inputs R which are used. A reset pulse on the reset input R causes all of the bits in a given stage to assume the binary value "0". The three reset inputs R are connected in common to a reset line. All of the clock inputs to all four stages of the shift register 36 are connected in common to a clock line. Clock pulses are applied to the clock line by a conventional position transducer (or other means of keeping track of the source position) each time the source advances ½ degree to irradiate a new peripheral detector. The number of bits in each stage corresponds to the number of detectors subtended by the radiation fan. Thus these bits are referred to as "detector bits". The detector bits B1 through B720 are consecutively numbered so that they correspond to the detectors 1 through 720 comprising the detector ring 22. (FIg. 2)

Figure 4:
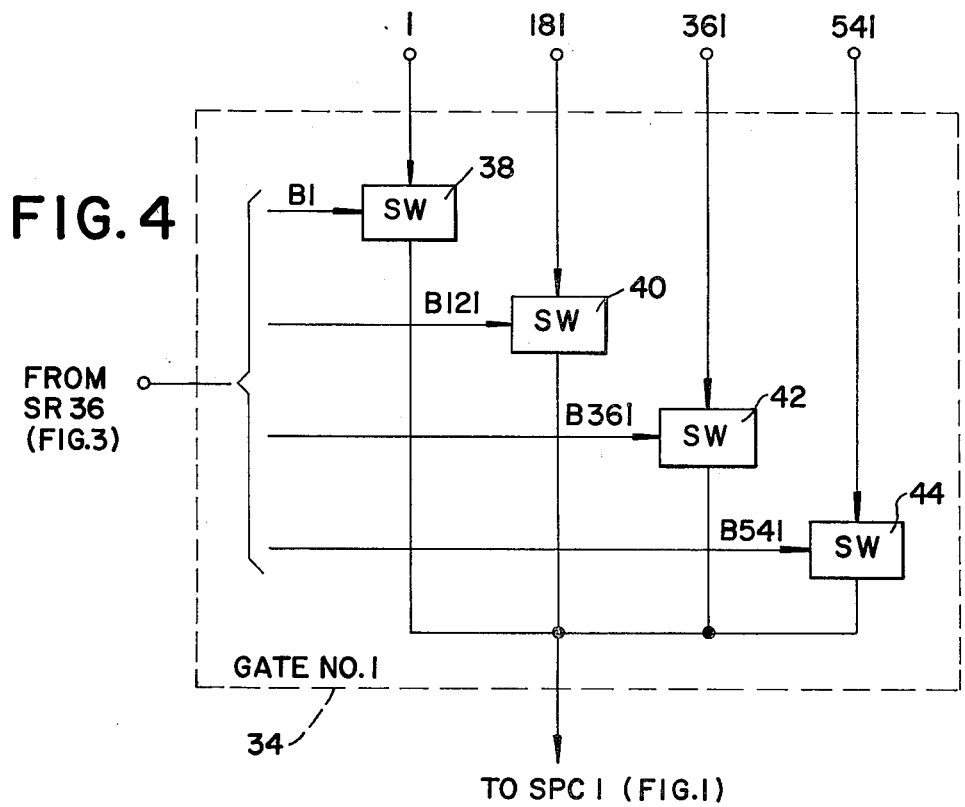
FIG. 4 is a block diagram illustrating one of the gates of FIG. 2 in more detail.

Each detector bit of a shift register stage has a corresponding output (sometimes referred to as Q) which represents a DC signal level or "logic level" corresponding to the binary value of the bit. The output of each bit is connected to actuate a corresponding switch in one of the gates 34. As shown in FIG. 4, gate No. 1 comprises four switches 38, 40, 42 and 44 independently controlled by the DC levels of the corresponding detector bits of the shift register 36. Switch 38 is connected to receive the analog output of detector No. 1. The output of switch 38 is effectively blocked when the detector bit B1 has the value "0". When the detector bit B1 assumes the value "1" the detector output is passed via the gate 38 to signal processing channel 1. Similarly, the switch 40 is connected to receive the analog output of detector 181 and to pass that output when the state of detector bit B181 is "1". Switches 42 and 44 operate similarly to pass the outputs of detectors 361 and 541. The outputs of the switches 38, 40, 42 and 44 connected in common signal processing channel No. 1.

In operation, at the start of the scan, when the X-ray fan beam strikes detectors 1 through 180 as shown in FIG. 2, the shift register 36 is "initialized" by applying set and reset pulses to the set and reset lines. This sets detector bits 1 through 180 comprising first stage of shift register 36 and clears bits 181 to 720 in the remaining three stages of the shift register 36. Since detector bits B1 through B180 have assumed the value "1", the switches for detectors 1 through 180, that is one switch in each gate 34, are turned on thus directly connecting the analog outputs of detectors 1 through 180 to the 180 processing channels 24. The set and reset pulse does not recur until the source is rotated through 360°. After the source is rotated $\frac{1}{2}$°, the radiation fan covers detectors 2 through 181. The $\frac{1}{2}$° rotation causes a clock pulse to appear on the common clock line to the shift register 36. The entire shift register is clocked once shifting 180 "1" bits to detector bit positions B2 through B181. It is as if a train 181 cars long is moved on the track a distance of one car length. Detector bit B1 returns to "0" because the zero value of detector bit B720 has now been shifted to the position of detector bit B1. In this condition, gate 1 now stops passing the output of detector 1 and passes the output of detector 181 to the first signal processing channel. Gates 2 through 180 continue to pass through the same detector outputs, namely, detectors 2 through 180.

After another rotation of $\frac{1}{2}$° and another clocking of the shift register 36, the 180 bit train is shifted to coincide with the detector bits B3 through B182. The last two bits, B181 and B182, are of course in the second stage of the shift register 36. Bits B1 and B2 of the first stage have now returned to "0". As a result, gate No. 2 stops passing the output of detector 2 and passes instead the output of detector 182 to the second signal processing channel. Gates No. 1 and gates Nos. 3 through 180 keep on passing the same detector outputs. After a third rotation of $\frac{1}{2}$° gate No. 3 ceases passing the output of detector 3 and passes instead the output of detector 183. The other gates do not change. This operation continues until the source has undergone 359$\frac{1}{2}$° of rotation at which time the beam subtends detector 720 and detectors 1 through 179. When the source reaches the starting position, the shift register is again initialized by asserting the set and reset lines to the shift register 36.

The system insures that 180 processing channels are always connected to the 180 detectors which are exposed to the X-ray fan. The "1" bits in the shift register track the detectors that are within the radiation fan and thus active detectors are time shared into a single channel. This multiplexing results in a 75% decrease in the amount of signal processing equipment which would otherwise have been required and thus lowers the cost of the system.

It is not critical that the number loaded into the first stage of the shift register 36 at the start of the scan be a series of binary "1's", although it seems to be highly preferable. Rather, a specific binary number comprising a series of "1's" and "0's" can be set into the first 180 bits of the shift register 36. It is only necessary that the switches in the gates 34 recognize the fact that any given time the output of the detector bit which corresponds to the switch indicates that the switch should be either open or closed.

In practice, the detector ring 22 may comprise an array of detectors spaced over an arc of less than 360 degrees, for example 212 degrees. In the 212 degree system, the source 20 moves clockwise to cover a 212 degree arc of detectors spaced at one degree intervals to complete a single scan. Source 20 is then moved back to the initial starting point to begin another scan. At the start of the scan, however, the fan beam is in a position such that one end of the arc of detectors intercepts only a portion of the fan beam; only approximately 32 detectors, namely detectors numbers 1 through 32 are irradiated. Likewise, at the end of the scan the last 32 detectors, namely 180 through 212 are irradiated. In the middle of the scan, the fan beam subtends approximately 80° or 80 detectors. Thus the maximum number of detectors subtended by the radiation fan is 80.

Implementing a system according to the invention for time sharing the signal processing channels by active detectors in the 212 degree system requires a slightly different arrangement of the shift register bits. At the start, only those bits corresponding to the first 32 detectors should have "on" state. However, after source rotation of 48°, the first 80 detector bits should have an "on" stage. To accomplish this, a nonclosed loop 260 bit shift register may be used with a series of 48 "dummy" bits preceding the 212 detector bits. Thus at the start of the scan, the first 80 bit positions of the shift register would be set to "1" and the remaining 180 bits of the shift register would be reset to "0". The 49th bit position of the shift register would correspond to detector 1 and the 260th bit position of the shift register would correspond to detector 212. For the first 48° of rotation, each degree of rotation would turn on another detector bit until all 80 detector bits were on. From this point on, the operation would be analogous to that of the system shown in FIG. 2, 3 and 4. Toward the end of the scan following the initial turning on of detector bit 212, the bits of the 80 bit train would in effect be pushed off the end of the shift register one at a time. An alternative way of implementing the present invention which avoids the use of 48 dummy bits at the beginning of the shift register would be to use a 212 bit shift register with one set line for only the first detector bit position. Detector bit No. 1 would be set to "1" at the start of the scan and restored to "1" with each one degree of rotation up to and including 80° of rotation of the source. When the source rotated to the 81st degree, the detector bit would, from that point on, fail to be restored and remain in the "off" state while the 80 bit train advanced through the shift register to track the active detectors.

The above disclosure is intended to be only illustrative and not restrictive. The scope of the invention is indicated by the appended claims and equivalents.

What is claimed is:

1. In a CT scanner having a series of stationary radiation detectors spaced in a curved path about a center point and a concentrically rotating fan pattern of radiation subtending a number of the detectors, the irradiated area common to different positions of the fan pattern defining a corresponding patient scan circle, a data channel multiplexing system comprising:
a number of gate means corresponding to the maximum number of detectors subtended by the fan pattern, each connected to receive the outputs of a respective exclusive group of non-consecutive detectors, one and only one of which is irradiated at any given time by the radiation fan, control means connected to each said gate means for selectively causing each said gate means to pass the output of only said one irradiated detector in each group, the output of each said gate means defining a corresponding signal processing channel.

2. The system of claim 1 wherein said control means comprises:

a shift register including a series of detector bits;

means for loading a predetermined binary number into a number of consecutive bits of said shift register, said consecutive bits corresponding to the maximum number of detectors subtended by the radiation fan; and clocking means responsive to advancement of the fan pattern of radiation for shifting said shift register;

for any given position of the fan pattern of radiation, each gate means permitting the passage of the output of only said one irradiated detector as determined by the state of the shift register detector bits corresponding respectively to the detectors in the group received by the particular gate means.

3. The system of claim 2 wherein each said gate means includes a group of switches corresponding respectively to the group of detector outputs, each of said switches being further connected to said shift register so as to be controlled by the state of the corresponding detector bit, the outputs of said switches being connected in common to define the corresponding signal processing channel.

4. In a CT scanner having a series of stationary radiation detectors spaced in a curved path about a center point and a concentrically rotating source of radiation emitted in a fan pattern subtending a number of the detectors each detector producing an electronic output signal having an amplitude indicative of the intensity of radiation impinging upon the detector, the irradiated area common to different positions of the fan pattern defining a corresponding patient scan circle, a data channel multiplexing system comprising:

a number of electronic signal passing means corresponding to the maximum number of detectors subtended by the fan pattern, each connected to receive the electronic output signals of a respective exclusive group of nonconsecutive detectors, one and only one of which is irradiated at any given time by the radiation fan, for passing the electronic output signal of one irradiated detector in each group, the output of each said passing means defining a corresponding signal processing channel.

5. The system of claim 1 wherein each passing means receives the electronic output signals of detectors spaced at approximately $2\pi\ p/n$ radian intervals, wherein n corresponds to the total number of detector positions available at a given spacing about the center and p corresponds to the maximum number of detectors subtended by the radiation fan.

* * * * *